(12) United States Patent
Bonrath et al.

(10) Patent No.: US 9,180,434 B2
(45) Date of Patent: Nov. 10, 2015

(54) CATALYTIC SYSTEM

(71) Applicant: DSM IP ASSETS B.V., Heerlen (NL)

(72) Inventors: Werner Bonrath, Basel (CH); Lioubov Kiwi-Minsker, Lausanne (CH); Igor Iouranov, Lausanne (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/350,951

(22) PCT Filed: Oct. 26, 2012

(86) PCT No.: PCT/EP2012/071221
§ 371 (c)(1),
(2) Date: Apr. 10, 2014

(87) PCT Pub. No.: WO2013/060821
PCT Pub. Date: May 2, 2013

(65) Prior Publication Data
US 2015/0005535 A1   Jan. 1, 2015

(30) Foreign Application Priority Data

Oct. 27, 2011 (EP) .................................... 11186918

(51) Int. Cl.
| | |
|---|---|
| *B01J 23/06* | (2006.01) |
| *B01J 23/66* | (2006.01) |
| *B01J 37/02* | (2006.01) |
| *B01J 37/08* | (2006.01) |
| *B01J 37/12* | (2006.01) |
| *B01J 37/18* | (2006.01) |
| *B01J 23/50* | (2006.01) |
| *B01J 35/00* | (2006.01) |
| *B01J 35/06* | (2006.01) |
| *C07C 29/17* | (2006.01) |
| *B01J 23/89* | (2006.01) |
| *B01J 27/138* | (2006.01) |

(52) U.S. Cl.
CPC *B01J 23/66* (2013.01); *B01J 23/50* (2013.01); *B01J 23/8953* (2013.01); *B01J 27/138* (2013.01); *B01J 35/006* (2013.01); *B01J 35/06* (2013.01); *B01J 37/0217* (2013.01); *B01J 37/0242* (2013.01); *B01J 37/0244* (2013.01); *B01J 37/08* (2013.01); *B01J 37/12* (2013.01); *B01J 37/18* (2013.01); *C07C 29/17* (2013.01); *C07C 2523/66* (2013.01)

(58) Field of Classification Search
CPC ............................. B01J 23/06; C23C 16/407
USPC ...................................... 568/903; 427/255.32
See application file for complete search history.

(56) References Cited

U.S. PATENT DOCUMENTS

| | | |
|---|---|---|
| 5,866,734 A | 2/1999 | Flick et al. |
| 6,388,150 B1 | 5/2002 | Overbeek et al. |
| 2012/0302801 A1 | 11/2012 | Bonrath et al. |

FOREIGN PATENT DOCUMENTS

| | | | |
|---|---|---|---|
| EP | 0 827 944 | 3/1998 | |
| WO | WO 00/43337 | 7/2000 | |
| WO | WO 2011/092280 | 8/2011 | |
| WO | WO-2011/092280 | * 8/2011 | ............. C07C 29/17 |

OTHER PUBLICATIONS

International Search Report for PCT/EP2012/071221 mailed 16 Jan. 2013.
Semagina et al., "Structured Catalyst of Pd/ZnO on Sintered Metal Fibers for 2-methyl-3-butyn-2-ol Selective Hydrogenation", Journal of Catalysis, vol. 251, No. 1, Sep. 7, 2007, pp. 213-222.

* cited by examiner

*Primary Examiner* — Kamal Saeed
*Assistant Examiner* — Janet L Coppins
(74) *Attorney, Agent, or Firm* — Nixon & Vanderhye P.C.

(57) ABSTRACT

The present invention relates to a structured catalyst based on sintered metal fibers (SMF) coated by a non-acidic metal oxide layer impregnated with Pd and Ag nanopartides, characterized in that the ratio of the Pd:Ag is 1:1 to 10:1, as well as the use of such a catalyst in selective catalytic hydrogenations of organic compounds.

24 Claims, No Drawings

CATALYTIC SYSTEM

This application is the U.S. national phase of International Application No. PCT/EP2012/071221 filed 26 Oct. 2012 which designated the U.S. and claims priority to EP 11186918.6 filed 27 Oct. 2011, the entire contents of each of which are hereby incorporated by reference.

The goal of the present invention was to find a structured catalyst with improved selectivity in semihydrogenation of organic starting material.

Catalytic semihydrogenations (=selective catalytic hydrogenations) of alkynols to alkenols are important processes in the fine chemicals industry. Pd-based catalysts are known to give the highest selectivity and yield. Preferential formation of olefinic alcohols is attributed to the stronger adsorption of acetylenic alcohols in comparison with the half-hydrogenation product. Catalytic performance of palladium is known to be strongly influenced by its dispersion, nature of support and the use of promoters and additives.

Due to the importance of such selective catalytic hydrogenations, there is always a need to improve these selective catalytic hydrogenations.

Surprisingly, it has been found that a structured catalyst based on sintered metal fibers (SMF) coated by a non-acidic metal oxide layer impregnated with Pd- and Ag-nanoparticles, shows improved properties in such selective catalytic hydrogenations.

Surprisingly, the selective catalytic hydrogenation using a structured catalyst according to the present invention can be carried out without any organic modifiers, which are usually used in such processes.

Such organic modifiers are organic bases comprising S and/or N atoms. Examples of such modifiers are 6-dithia-1, 8-octandiol, thiophene, dipropyl sulfide, tetrahydrothiophene, quinoline, pyridine and diethylaminoethanol.

Therefore, the present invention relates to a structured catalyst based on sintered metal fibers (SMF) coated by a non-acidic metal oxide layer impregnated with Pd- and Ag-nanoparticles, characterized in that the ratio of the Pd:Ag-nanoparticles is 1:1 to 10:1.

The term "structured catalyst" as used herein refers to catalysts wherein the spatial position of the catalyst is controlled. Structured catalysts are known in the art, see, e.g., Chimia 56(4), 2002, 159-163. Examples of structured catalysts are ceramic carrier constructions and fibrous structures, especially filamentous (woven or not) materials. All types of filamentous materials can be used in the present invention. The fibers may be from organic or inorganic matter. Examples are: fabrics from activated carbon fibers, glass fibers, ceramic fibers, composite oxides fibers, and metal fibers filters or fleece. Preferred are metal fiber materials. The individual fibers of these materials preferably have a diameter of about 2 µm to about 100 µm, especially a diameter of no more than about 20 µm. The materials may be chemically treated, to modify the specific surface area and/or may have a coating, e.g. of metal oxides such as Al, Ti, Mg, Zn, etc.

Furthermore the SMF can also comprise an alloy wherein the alloy is free from Al. Preferably such an alloy is stainless steel.

Furthermore, the SMF can consist of a FeCrAl alloy, which optionally can be pre-oxidised.

The metal oxide layer, which coats the SMF, is non-acidic. The metal oxide layer is basic or amphoteric. Suitable non-acidic metal oxide layers comprise Zn, Cr, Mn, Cu or Al. Preferably the metal oxide layer comprises ZnO and optionally at least one further metal oxide wherein the metal is chosen from the group consisting of Cr, Mn, Mg, Cu and Al.

The SMF are preferably coated with a thin layer of ZnO and optionally at least one further metal (Cr, Mn, Mg, Cu and Al) oxide.

The coating of the SMF is done by commonly known processes, such as i.e. dip-coating.

In a preferred embodiment the ZnO layer is a grain-structured ZnO layer.

Usually the catalyst of the present invention comprises between 0.01 and 20 weight-% (wt-%), based on the total weight of the catalyst, of ZnO, preferably between 0.1 and 10 wt-%, more preferably between 1.5 and 10 wt-% and most preferably between 2 and 8 wt-%.

The coated SMF are then impregnated by Pd- and Ag-nanoparticles. The nanoparticles are synthesized by commonly known methods, for example by the precursor solution reduction using i.e. poly(N-vinyl-2-pyrrolidone) or $Na_2MoO_4$ as stabilizers.

Usually the Pd-nanoparticles, which are on the non-acidic metal oxide layer, have an average particle size of between 0.5 and 20 nm, preferably of between 2 and 15 nm, more preferably of between 5 and 12 nm and most preferably of between 7 to 10 nm.

Usually the Ag-nanoparticles, which are on the non-acidic metal oxide layer, have an average particle size of between 0.5 and 10 nm, preferably of between 2 and 10 nm, more preferably of between 5 and 10 nm and most preferably of between 7 to 10 nm.

Preferably the Pd- and the Ag-nanoparticles have similar average particle sizes. The ratio of the Pd- and Ag-nanoparticles deposited on the non-acidic metal oxide layer is going from 1:1 to 10:1.

Preferably the ratio of the Pd- and Ag-nanoparticles goes from 1.5:1 to 8:1, more preferably from 2:1 to 5:1.

The catalyst according to present invention comprises between 0.001 and 5 wt-%, based on the total weight of the catalyst, of the Pd- and Ag-nanoparticles, preferably between 0.01 and 2 wt-% more preferably between 0.05 and 1 wt-% and most preferably between 0.1 and 0.3 wt-%.

The catalyst can also comprise further metals. These co-metals are i.e. Pb, Mn, Cu, Bi, Sn, Au, Zn and Cd.

The catalyst is usually activated before the use. The activation is done by using well known processes.

The catalyst of the present invention is used in selective catalytic hydrogenation of organic starting material, especially of organic starting material comprising a carbon-carbon triple bond, more especially of alkynol compounds.

A preferred embodiment is a structured catalyst (SC), based on sintered metal fibers coated by an amphoteric or basic metal oxide layer comprising between 0.01 and 20 wt-%, based on the total weight of the catalyst, of ZnO and optionally at least one further metal oxide, wherein the metal is chosen from the group consisting of Cr, Mn, Mg, Cu and Al, and impregnated by Pd- and Ag-nanoparticles, wherein the ratio of the Pd:Ag-nanoparticles deposited on the amphoteric or basic metal oxide layer goes from 1:1 to 10:1, and wherein SC comprises between 0.001 and 5 wt-%, based on the total weight of the catalyst, of the Pd- and Ag-nanoparticles.

It is preferred that the ZnO layer of SC is grain structured.

It is also preferred that the average particle size of the Pd- and Ag-nanoparticles of SC is between 0.5 to 20 nm (more preferred 2 to 15 nm, even more preferred 5 to 12 nm, most preferred 7 to 10 nm).

Furthermore it is preferred that the Pd and Ag-nanoparticles of SC have the same average particle sizes.

A more preferred embodiment is a structured catalyst (SC'), based on sintered metal fibers coated by an amphoteric or basic metal oxide layer comprising between 0.1 and 10 wt-%, based on the total weight of the catalyst, of ZnO and optionally at least one further metal oxide, wherein the metal is chosen from the group consisting of Cr, Mn, Mg, Cu and Al, and impregnated by Pd- and Ag-nanoparticles, wherein the ratio of the Pd:Ag-nanoparticles deposited on the amphoteric or basic metal oxide layer goes from 1.5:1 to 8:1 and wherein SC' comprises between 0.01 and 2 wt-%, based on the total weight of the catalyst, of the Pd- and Ag-nanoparticles.

It is preferred that the ZnO layer of SC' is grain structured.

It is also preferred that the average particle size of the Pd- and Ag-nanoparticles of SC' is between 0.5 to 20 nm (more preferred 2 to 15 nm, even more preferred 5 to 12 nm, most preferred 7 to 10 nm).

Furthermore it is preferred that the Pd and Ag-nanoparticles of SC' have the same average particle sizes.

An even more preferred embodiment is a structured catalyst (SC''), based on sintered metal fibers coated by an amphoteric or basic metal oxide layer comprising between 1.5 and 10 wt-%, based on the total weight of the catalyst, of ZnO and optionally at least one further metal oxide, wherein the metal is chosen from the group consisting of Cr, Mn, Mg, Cu and Al, and impregnated by Pd- and Ag-nanoparticles, wherein the ratio of the Pd:Ag-nanoparticles deposited on the amphoteric or basic metal oxide layer goes from 2:1 to 5:1 and wherein SC'' comprises between 0.05 and 1 wt-%, based on the total weight of the catalyst, of the Pd- and Ag-nanoparticles.

It is preferred that the ZnO layer of SC'' is grain structured.

It is also preferred that the average particle size of the Pd- and Ag-nanoparticles of SC'' is between 0.5 to 20 nm (more preferred 2 to 15 nm, even more preferred 5 to 12 nm, most preferred 7 to 10 nm).

Furthermore it is preferred that the Pd and Ag-nanoparticles of SC'' have the same average particle sizes.

A most preferred embodiment is a structured catalyst (SC'''), based on sintered metal fibers coated by an amphoteric or basic metal oxide layer comprising between 2 and 8 wt-%, based on the total weight of the catalyst, of ZnO and optionally at least one further metal oxide, wherein the metal is chosen from the group consisting of Cr, Mn, Mg, Cu and Al, and impregnated by Pd- and Ag-nanoparticles, wherein the ratio of the Pd:Ag-nanoparticles deposited on the amphoteric or basic metal oxide layer goes from 2:1 to 5:1 and wherein SC''' comprises between 0.1 and 0.3 wt-%, based on the total weight of the catalyst, of the Pd- and Ag-nanoparticles.

It is preferred that the ZnO layer of SC''' is grain structured.

It is also preferred that the average particle size of the Pd- and Ag-nanoparticles of SC''' is between 0.5 to 20 nm (more preferred 2 to 15 nm, even more preferred 5 to 12 nm, most preferred 7 to 10 nm).

Furthermore it is preferred that the Pd and Ag-nanoparticles of SC''' have the same average particle sizes.

The selective catalytic hydrogenations using the structured catalysts as described above are carried without any organic modifiers.

It is surprising that an improved selectivity of the selective catalytic hydrogenations is obtained. The selectivity of such a selective catalytic hydrogenation is better than the one obtained by a catalyst comprising Pd-nanoparticles only (or a very high amount of Pd) or the one obtained by a catalyst comprising Au-nanoparticles instead of Ag-nanoparticles.

Therefore, the present invention also relates to a process (P) of reacting a compound of formula (I)

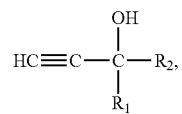

(I)

wherein $R_1$ is linear or branched $C_5$-$C_{35}$ alkyl or linear or branched $C_5$-$C_{35}$ alkenyl moiety, wherein the C-chains can be substituted, and $R_2$ is linear or branched $C_1$-$C_4$ alkyl, wherein the C-chain can be substituted, with hydrogen in the presence of (i) a structured catalyst based on sintered metal fibers (SMF) coated by a non-acidic metal oxide layer impregnated with Pd- and Ag-nanoparticles, characterized in that the ratio of the Pd:Ag-nanoparticles is 1:1 to 10:1.

A compound of formula (Ia)

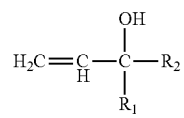

(Ia)

wherein all the substituents have the same meanings as defined for the compound of formula (I) is the obtained reaction product of this process (P).

The process is usually (and preferably) carried out without any organic modifiers.

Therefore a further embodiment of the present invention relates to a process (P') as described above, wherein no organic modifier is used.

In a preferred process (P'') compounds of formula (I), wherein $R_1$ is a linear or branched $C_5$-$C_{30}$ alkyl moiety or a linear or branched $C_5$-$C_{30}$ alkenyl moiety, wherein the C-chain can be substituted, and $R_2$ is a linear or branched $C_1$-$C_4$ alkyl moiety, wherein the C-chain can be substituted, are used.

In a more preferred process (P''') compounds of formula (I), wherein $R_1$ is a linear or branched $C_6$-$C_{16}$ alkyl moiety or a linear or branched $C_6$-$C_{16}$ alkenyl moiety, wherein the C-chain can be substituted, and $R_2$ is a $C_1$-$C_2$ alkyl moiety, wherein the C-chain can be substituted, are used.

In a most preferred process (P'''') compounds of formula (I), wherein $R_1$ is a linear or branched $C_6$-, $C_{11}$- or $C_{16}$-alkyl moiety or a linear or branched $C_6$-, $C_{11}$- or $C_{16}$-alkenyl moiety, and $R_2$ is a $C_1$-$C_2$ alkyl moiety, are used.

Preferred are processes (P), (P'), (P''), (P''') and (P''''), wherein SC is used as a catalyst.

More preferred are processes (P), (P'), (P''), (P''') and (P''''), wherein SC' is used as a catalyst.

Even more preferred are processes (P), (P'), (P''), (P''') and (P''''), wherein SC'' is used as a catalyst.

Most preferred are processes (P), (P'), (P''), (P''') and (P''''), wherein SC''' is used as a catalyst.

Especially preferred is the selective catalytic hydrogenation of dehydroisophytol (DIP)

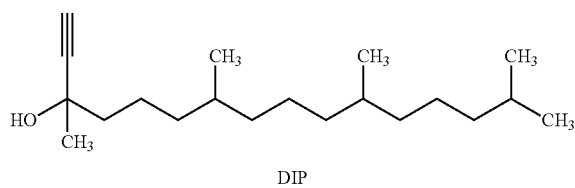

DIP to isophytol (IP)

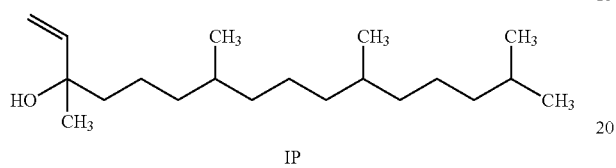

IP using a structured catalyst (SC, SC', SC" or SC''') as disclosed above.

Also especially preferred is the selective catalytic hydrogenation of dehydrolinalool (DLL)

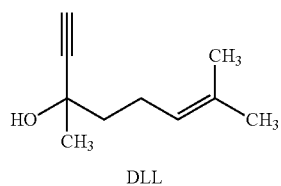

DLL to linalool (LL)

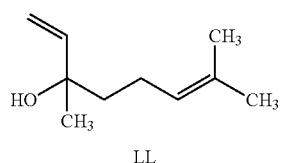

LL using a structured catalyst (SC, SC', SC" or SC''') as disclosed above.

For both of these reactions, all the preferences for the structured catalyst apply. Preferably SC, more preferably SC', even more preferably SC" and most preferably SC''' are used in these processes.

The selective catalytic hydrogenation in accordance with the present invention can be carried out under conditions conventionally used for hydrogenations. Suitably, the selective catalytic hydrogenation is carried out at a pressure of about 0.1 to about 6 MPa and at a temperature of about 250 K to about 500 K. The selective catalytic hydrogenation can be carried out batch wise or in continuous mode.

Preferably, the pressure used for the selective catalytic hydrogenation is between 1.1 and 30 bar, more preferably between 1.1 and 15 bar, even more preferably between 1.5 and 10 bar and most preferably between 2 and 8 bar.

Preferably, the reaction temperature for the selective catalytic hydrogenation is between 250 K and 420 K, more preferably between 273 K and 380 K, even more preferably between 274 K and 350 K and most preferably between 295 and 335 K.

The selective catalytic hydrogenation can be carried out with or without a solvent.

The reaction products obtained by these selective catalytic hydrogenations are useful intermediates in the synthesis of a vitamins, carotenoids, perfume ingredients, and/or food ingredients.

The following examples serve to illustrate the invention. All parts and percentages are related to weight (if not otherwise stated) and the temperature is given in degree Celsius (if not otherwise stated).

EXAMPLES

Catalyst Preparation

Example 1

0.2% Pd(Ag)/5% ZnO/SMF (Pd:Ag Molar Ratio=3.5)

Materials

Sintered Metal Fibers ($SMF_{Fecral}$), Fecralloy, 40FP3 are available from Southwest Screen & Filters SA (now Bekaert SA, Belgium).

All used chemicals (>99%) were purchased from Aldrich and used as received. All gases (>99.5%) were supplied by Carbagas.

Step 1: Pre-treatment

In order to remove contaminations, $SMF_{Fecral}$ panels (10× 10 cm, m=6-7 g) were treated in boiling toluene for 0.5 h and air-dried. $SMF_{Fecral}$ were then oxidized in air at 600° C. for 3 hours. After cooling down to room temperature, treated $SMF_{Fecral}$ were stored in a dry atmosphere.

Step 2: Support Coating with Zn Oxide

The $SMF_{Fecral}$ panels cleaned as described in Step 1 were dip-coated by a Zn oxide layer. A ZnO precursor solution was prepared as following: 18.3 g of monoethanolamine and 12.8 g of acetoin are dissolved in 0.75 L of i-propanol. Then, 65.8 g of $Zn(CH_3COO)_2.2H_2O$ were added to the mixture and dissolved under stirring.

ZnO layer deposition was performed by dipping $SMF_{Fecral}$ panels into the ZnO precursor solution followed by its drying in air at room temperature (0.5 h) and calcination at 600° C. (0.5 h). The dipping-drying-calcination cycle was repeated 6 times to deposit ~5 wt. % of ZnO. Coated $SMF_{Fecral}$ panels were then post-annealed at 900° C. for 15 min. The prepared 5% $ZnO/SMF_{Fecral}$ were stored in a dry atmosphere.

Step 3: Synthesis of Pd(Ag) Nanoparticles and Deposition of the Pd(Ag) Nanoparticles Pd-nanoparticles sol was prepared as following: 0.277 g of poly(N-vinyl-2-pyrrolidone) (K 30, M~50000) and 0.156 g of ascorbic acid were dissolved in 15 ml of hot (95-98° C.) water (Solution 1). In another beaker, 0.088 g of $PdCl_2$ and 0.058 g of NaCl were dissolved in 10 ml of hot water (Solution 2). Solution 2 was added fast to Solution 1 under stirring. The solution color changed immediately from brown to black indicating Pd nanoparticles formation. The obtained colloid solution was kept under stirring and heating for 3 hours. Then, the sol was cooled down and diluted by 75 ml of acetone. The mixture was left for the night without stirring. The colorless liquid phase was discarded. The black viscous residue was dissolved in 12.5 ml of water giving a stable Pd sol.

In order to modify the synthesized Pd nanoparticles by Ag (Pd:Ag molar ration=3.5:1), Solution 3 was prepared as following: 0.026 g of KAg(CN)$_2$ were dissolved in 1 ml of water and 0.03 g of 20% aqueous N$_2$H$_4$ were added. Solution 3 was added fast under stirring to the prepared Pd sol. The final solution was kept under stirring for 2 hours. The prepared Pd/Ag(3.5:1) sol was stable during months. ZnO coated SMF$_{FeCrAl}$ panels (2 pieces, 10×10 cm, ~14 g) were impregnated by the prepared Pd/Ag(3.5:1) sol and dried in air at room temperature. The impregnation-drying cycle was repeated 2 times in order to reach a 0.2 wt. % Pd loading.

Step 4: Post-treatment/Activation

The 0.2% Pd(Ag)/5% ZnO/SMF$_{FeCrAl}$ panels were calcined in air at 600° C. (2 hours) and then reduced in a 10% H$_2$+90% Ar flow (flow rate—450 ml/min) at 300° C. (2 hours). Sometimes, in order to improve the catalyst performance, the oxidation-reduction cycle was repeated several times.

Example 2

0.2% Pd(Au)/5% ZnO/SMF (Pd:Ag Molar Ratio=3.5)

This catalyst was prepared in analogy to the catalyst of example 1 with the exemption that instead of KAg(CN)$_2$ an equimolar amount of KAu(CN)$_2$ was used.

Hydrogenation process

Hydrogenation of Dehydroisophytol (DIP) to Isophytol (IP) with the Catalyst of Example 1

In a 500 ml stainless steel autoclave, equipped with a stirrer, temperature- and pressure-control, about 0.8 g catalyst of example 1 and 70 g DIP was added. The reactor was heated under hydrogen pressure to 95° C. and 4 bar (absolute pressure) and the reaction mixture was stirred (with 2000 rpm). At the end (x=99%) as well as during the reaction (x=50% and x=95%), the crude reaction product was collected and analyzed.

The selectivity for this hydrogenation measured at x=50% was 96.5%.

The selectivity for this hydrogenation measured at x=95% was 96.0%.

The selectivity for this hydrogenation measured at x=99% was 94.4%.

Hydrogenation of Dehydroisophytol (DIP) to Isophytol (IP) with the Catalyst of Example 2

In a 500 ml stainless steel autoclave, equipped with a stirrer, temperature- and pressure-control, about 0.8 g catalyst of example 2 and 70 g DIP was added. The reactor was heated under hydrogen pressure to 95° C. and 4 bar (absolute pressure) and the reaction mixture was stirred (with 2000 rpm). At the end (x=99%) as well as during the reaction (x=50% and x=95%), the crude reaction product was collected and analyzed.

The selectivity for this hydrogenation measured at x=50% was 95.9%.

The selectivity for this hydrogenation measured at x=95% was 86.4%.

The selectivity for this hydrogenation measured at x=99% was 76.0%.

Hydrogenation of Methylbutynol (MBY), Discontinuously (=Batch-wise)

In a 500 ml stainless steel autoclave, equipped with a stirrer, temperature- and pressure-control, about 1.5 g catalyst of example 1 and 285 g MBY was added. The reactor was heated under hydrogen pressure to 65° C. and 4 bar (absolute pressure) and the reaction mixture was stirred (with 1050 rpm). At the end (x=99%) as well as during the reaction, the crude reaction product was collected and analyzed.

The selectivity for this hydrogenation measured at x=99% was 90%.

Hydrogenation of Methylbutynol (MBY), Continuously

MBY (46.6 g) and MBE (187 g) were added to a 500 mL-reactor (this mixture was employed in order to start the reaction at 80% conversion). Into a metal grid basket which was attached to the gas entrainment impeller were put 6 SMF catalyst strips (0.2% Pd(Ag)/5% ZnO/SMF$_{Fecraloy}$) with a total weight of 1.77 g. Subsequently, the reactor was pressurized 3 times with 4 bar H$_2$. After the pressure was released, the stirred (500 rpm) reaction mixture was heated to 65° C. Subsequently, the reaction was started by stirring the mixture at 1700 rpm. The MBY feed and the product flow were adjusted such that the weight of the reactor remained constant and the conversion was about 80% during the course of the hydrogenation. Samples were taken and analyzed by GC to monitor the reaction.

Conversion: 82%
Selectivity: 93%
Reaction time 300 h:

Hydrogenation of Dehydrolinalool (DLL), Discontinuously

DLL (285 g, 1.87 Mol) was added to a 500 mL-reactor. Into a metal grid basket which was attached to the gas entrainment impeller were put 6 SMF catalyst strips (0.2% Pd(Ag)/5% ZnO/SMF$_{Fecraloy}$) with a total weight of 1.49 g. Then the reactor was closed and pressurized 3 times with 4 bar N$_2$. After the pressure was released, the stirred (400 rpm) reaction mixture was heated to 65° C. When 65° C. was reached the stirrer was stopped and the reactor was pressurized 4 times with 4 bar H$_2$. Subsequently, the reaction was started by stirring the mixture at 1050 rpm. Samples were taken at 120 and 1678 minutes and analyzed by GC to monitor the reaction.

TABLE

Results of the discontinuous hydrogenation of DLL to LL

| Reaction time [min] | Activity [mmol H$_2$ * s$^{-1}$ * g$^{-1}$] | Conversion [%] | Selectivity [%] |
|---|---|---|---|
| 120 | 15.8 × 10$^{-3}$ | 7.2 | 96 |
| 1678 | 13.6 × 10$^{-3}$ | 95.6 | 96 |

The invention claimed is:

1. A structured catalyst based on sintered metal fibers (SMF) coated by a non-acidic metal oxide layer impregnated with Pd-nanoparticles and Ag-nanoparticles, wherein a ratio of Pd-nanoparticles: Ag-nanoparticles is 1:1 to 10:1, and wherein the SMF consists of an alloy free from Al.

2. The structured catalyst according to claim 1, wherein the alloy is stainless steel.

3. The structured catalyst according to claim 1, wherein the non-acidic metal oxide layer comprises ZnO and optionally at least one further metal oxide selected from the group consisting of Cr, Mn, Mg, Cu and Al.

4. The structured catalyst according to claim 1, wherein the structured catalyst comprises between 0.01 and 20 wt. %, based on the total weight of the catalyst, of ZnO.

5. The structured catalyst according to claim 1, wherein the Pd-nanoparticles have an average particle size of between 0.5 and 20 nm.

6. The structured catalyst according to claim 1, wherein the Ag-nanoparticles have an average particle size of between 0.5 and 10 nm.

7. The structured catalyst according to claim 1, wherein the ratio of the Pd-nanoparticles:Ag-nanoparticles is from 1.5 : 1 to 8:19.

8. The structured catalyst according to claim 1, wherein the structured catalyst comprises between 0.001 and 5 wt. %, based on the total weight of the catalyst, of the Pd-nanoparticles and the Ag-nanoparticles.

9. The structured catalyst according to claim 1, wherein the structured catalyst comprises between 0.1 and 10 wt. %, based on the total weight of the catalyst, of ZnO.

10. The structured catalyst according to claim 1, wherein the structured catalyst comprises between 1.5 and 10 wt. %, based on the total weight of the catalyst, of ZnO.

11. The structured catalyst according to claim 1, wherein the structured catalyst comprises between 2 and 8 wt. %, based on the total weight of the catalyst, of ZnO.

12. The structured catalyst according to claim 1, wherein the Pd-nanoparticles have an average particle size of between 2 and 15 nm.

13. The structured catalyst according to claim 1, wherein the Pd-nanoparticles have an average particle size of between 5 and 12 nm.

14. The structured catalyst according to claim 1, wherein the Pd-nanoparticles have an average particle size of between 7 and 10 nm.

15. The structured catalyst according to claim 1, wherein the Ag-nanoparticles have an average particle size of between 2 and 10 nm.

16. The structured catalyst according to claim 1, wherein the Ag-nanoparticles have an average particle size of between 5 and 10 nm.

17. The structured catalyst according to claim 1, wherein the Ag-nanoparticles have an average particle size of between 7 and 10 nm.

18. The structured catalyst according to claim 1, wherein the ratio of the Pd-nanoparticles: Ag-nanoparticles is from 2:1 to 5:1.

19. The structured catalyst according to claim 1, wherein the structured catalyst comprises between 0.01 and 2 wt. %, based on the total weight of the catalyst, of the Pd-nanoparticles and the Ag- nanoparticles.

20. The structured catalyst according to claim 1, wherein the structured catalyst comprises between 0.05 and 1 wt. %, based on the total weight of the catalyst, of the Pd-nanoparticles and the Ag- nanoparticles.

21. The structured catalyst according to claim 1, wherein the structured catalyst comprises between 0.1 and 0.3 wt. %, based on the total weight of the catalyst, of the Pd-nanoparticles and the Ag- nanoparticles.

22. A hydrogenation process which comprises contacting a compound of formula (I):

wherein

R$_1$ is linear or branched C$_5$-C$_{35}$ alkyl or linear or branched C$_5$-C$_{35}$ alkenyl moiety, wherein the C-chains can be substituted, and R$_2$ is linear or branched C$_1$-C$_4$ alkyl, wherein the C-chain can be substituted, with hydrogen in the presence of a catalyst according to claim 1.

23. The hydrogenation process according to claim 22, wherein no organic modifier is used.

24. The hydrogenation process according to claim 22, wherein the process is carried out under hydrogenation conditions at a pressure of about 0.1 to about 6 MPa and at a temperature of about 250 K to about 500 K.

* * * * *